(12) United States Patent
Bonnet

(10) Patent No.: US 6,336,048 B1
(45) Date of Patent: *Jan. 1, 2002

(54) IMPLANTABLE ACTIVE MEDICAL DEVICE ENSLAVED TO AT LEAST ONE PHYSIOLOGICAL PARAMETER

(75) Inventor: Jean-Luc Bonnet, Montrouge (FR)

(73) Assignee: Ela Medical S.A., Montrouge (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/198,384

(22) Filed: Nov. 24, 1998

(30) Foreign Application Priority Data

Nov. 25, 1997 (FR) .......................................... 97 14796

(51) Int. Cl.[7] .............................................. A61N 1/365
(52) U.S. Cl. ......................................... 607/19; 607/18
(58) Field of Search ............................. 607/18, 19, 17, 607/20

(56) References Cited

U.S. PATENT DOCUMENTS

| | | | | |
|---|---|---|---|---|
| 4,945,909 A | * | 8/1990 | Fearnot et al. | ................. 607/19 |
| 5,562,711 A | * | 10/1996 | Yerich et al. | ................. 607/18 |
| 5,626,622 A | * | 5/1997 | Cooper | ........................ 607/18 |
| 5,722,996 A | * | 3/1998 | Bonnet et al. | ................. 607/17 |

FOREIGN PATENT DOCUMENTS

| | | | |
|---|---|---|---|
| EP | 0 702 980 | 3/1996 | .......... A61N/1/365 |
| EP | 0 750 920 | 1/1997 | .......... A61N/1/365 |
| WO | WO 96 16695 | 6/1996 | .......... A61N/1/365 |

* cited by examiner

*Primary Examiner*—George R. Evanisko
(74) *Attorney, Agent, or Firm*—Orrick, Herrington & Sutcliffe, LLP

(57) ABSTRACT

An active implantable medical device, notably a cardiac pacemaker, enslaved to at least a physiological parameter which comprises at least one effort sensor (MV) having a plurality of determinable states, for measuring a primarily physiological parameter and delivering a signal which is a function of effort exerted by a patient bearing the device and at least one activity sensor (G) having a plurality of determinable states, for measuring a primarily physical parameter and delivering a signal which is indicative of the activity of the patient bearing the device. The determinable states of the respective sensors are determined and the relative sequence of successive changes in the state of the respective sensors are identified and analyzed periodically according to predetermined criteria. A command escape interval ($IE_{CONSIG}$) controlling the enslaved functioning of the device is determined from the analyzed states of the sensors. The command escape interval ($IE_{CONSIG}$) is then limited to predetermined values as appropriate.

14 Claims, 6 Drawing Sheets

US 6,336,048 B1

IMPLANTABLE ACTIVE MEDICAL DEVICE ENSLAVED TO AT LEAST ONE PHYSIOLOGICAL PARAMETER

FIELD OF THE INVENTION

The present invention is directed to "active implantable medical devices" such as those defined by the Jun. 20, 1990 directive 90/385/EEC of the European Community Council, and more particularly, to cardiac pacemakers and/or defibrillators, having a function that is enslaved to, i.e. responsive to, a parameter sensed by a sensor. Although the following description refers mainly to the case of a cardiac pacemaker, the invention also is applicable in a general manner to a great variety of electronic devices having a control function that is responsive to a sensed parameter.

BACKGROUND OF THE INVENTION

Active implantable medical devices are known to adapt their actions, for example, a control function such as the stimulation frequency in the case of a cardiac pacemaker, to the measured or calculated value of a parameter representative of the metabolic needs (cardiac output requirements) of the patient bearing the device.

EP 0 750 920 (and corresponding U.S. Pat. No. 5 722 996, which are both commonly owned by the assignee hereof, Ela Medical, and which are both incorporated herein by reference) describes the utilization of two sensors in a cardiac pacemaker, an activity sensor and an effort sensor, and proposes particularly a method to select the most rapid (in terms of response) sensor at the onset and at the end of an effort exerted by the patient, and the physiological sensor during the effort.

A "cross control" takes place to the extent that one sensor alone determining an effort, unconfirmed by the second, will not be taken into account except during a predetermined time (typically 15 seconds for the activity sensor and 2 minutes for the effort sensor). During an effort confirmed by both of the two sensors, enslavement will be based solely on the effort sensor (that is to say the sensor taken into account preferentially during the effort is the effort sensor) without control by the activity sensor.

According to the basic principle of enslavement set forth in EP 0 750 920 (which is implemented in the "TALENT 213" pacemaker available from ELA MEDICAL, the assignee hereof), an escape interval is calculated for the activity sensor every 1.5625 seconds which corresponds to new information of the sensor (i.e. update or refresh rate of the sensor information). Every four cardiac cycles, the former is averaged on the last four escape intervals. The escape interval is calculated for the effort sensor every respiratory cycle. Every four cardiac cycles, the former is averaged on the last eight escape intervals.

Values of the escape interval of the effort sensor and the activity sensor allow determination of states of the sensors. The two sensors calculate independently an escape interval. From the evolution of escape intervals, a state is defined for each sensor. There are three states:

| | |
|---|---|
| First state - REST | the sensor determines a rest state of the patient; |
| Second state - EFFORT | the sensor determines a state of "increasing" effort by the patient; |
| Third state - RECOVERY | the sensor determines an end of effort, which is an intermediate state between the effort state and the rest state. |

Given that there are two sensors and three states for each sensor, there are nine (in combination) states possible. For each (combination) state, the pacemaker adopts a different behavior. Each combination determines a value of the command escape interval, that is to say the escape interval to which the period of enslavement is tied. While enslavement with double sensors, such as that described previously and the object of the EP 0 750 920, is mainly based on the information provided by the effort sensor, it can happen that the escape interval defined by this sensor is not in concordance with the level of activity of the patient, in the case, for example, of significant movements. In this case, the command escape interval and the period of enslavement can have values not corresponding to the needs of the patient, being either too low or too high.

OBJECTS AND SUMMARY OF THE INVENTION

One of the objects of the present invention is to solve the foregoing problems and to define control of the command escape interval in the case where it is equal to the escape interval defined by the effort sensor. The present invention is directed to an active implantable medical device capable of enslaved functioning to at least one physiological parameter.

The device of the present invention comprises at least one effort sensor for measuring a primarily physiological parameter and delivering a signal which is a function of the effort exerted by a patient bearing the device, at least one activity sensor for measuring a primarily physical parameter and delivering a signal which is indicative of activity of the patient bearing the device, means for analyzing periodically the relative sequence of successive state changes of the sensors according to predetermined criteria intrinsic to the device, means for determining a command escape interval controlling the enslaved functioning of the device from the analyzed sensor states, and means for limiting the command escape interval to predetermined values.

According to one embodiment, limitations of the command escape interval are a function of the activity sensor escape interval.

According to another embodiment, limitations of the command escape interval correspond to the subtraction of a predefined constant percentage of the activity sensor escape interval.

Preferably, one applies two limitations, a lower limit and an upper limit, to the command escape interval.

Additionally, in an advantageous manner, the lower and upper limits are (re)defined each time that the means for analysis of the states of the sensors determines that the activity sensor escape interval is modified.

According to another embodiment, the means for limiting the command escape interval apply the limitation to the command escape interval only where the effort sensor is in a state other than the rest state.

Preferably, the means for limiting the command escape interval limits the enslavement frequency where the effort sensor detects an effort not detected by the activity sensor.

BRIEF DESCRIPTION OF THE DRAWINGS

Further features, characteristics and advantages of the invention will be understood by those persons of ordinary skill in the art in view of the following detailed description of a preferred embodiment of the present invention, made with reference to the drawings annexed hereto in which.

DETAILED DESCRIPTION OF THE DRAWINGS

In the detailed description that follows, the example of a cardiac pacemaker enslaved to a physiological parameter is discussed. This description, however, is not intended to be restrictive, and the teachings of the invention are directly applicable to other types of active implantable medical devices. Similarly, although the example refers to two sensors only, one can anticipate a more elaborate version having a greater number of sensors, multiplexed or otherwise combined between them, allowing to enslave the functioning of the device to a plurality of different physiological and/or physical parameters. Further, the sensor types described here (namely a Minute-Ventilation sensor for the effort sensor and an acceleration sensor for the activity sensor) are merely for purposes of illustration and not restrictive, and the use of other types of sensors can be envisaged.

Figure 1:
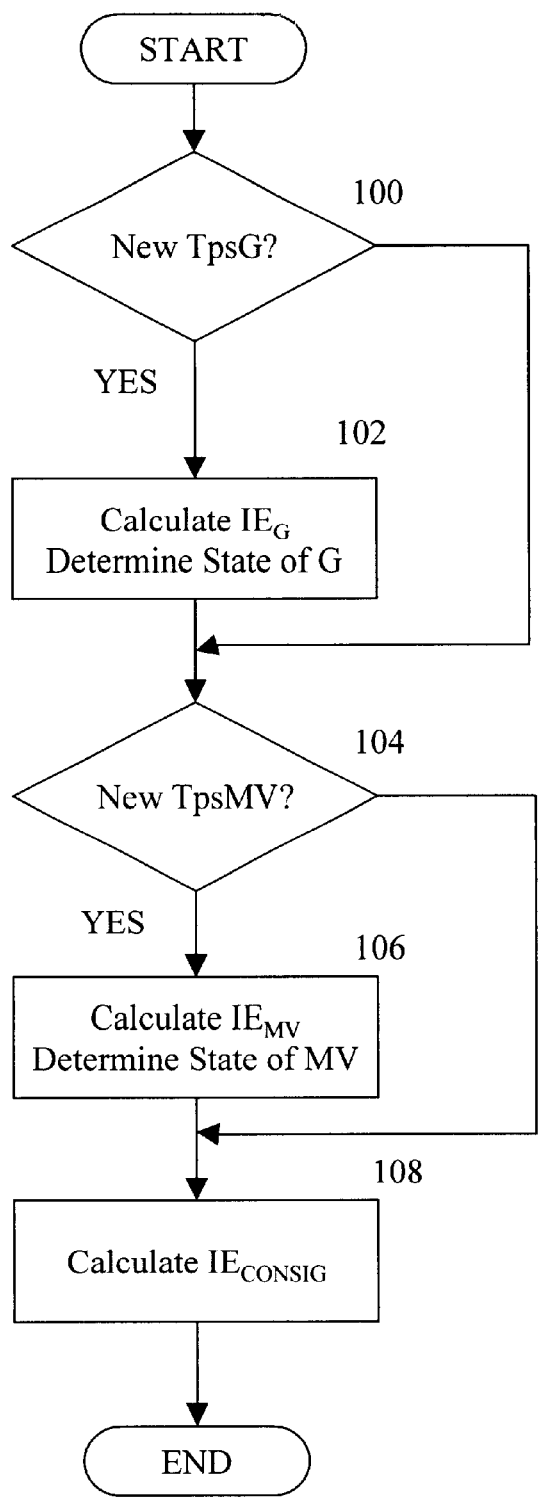
FIG. 1 illustrates a flow chart of the calculation of the command escape interval as is known.

FIG. 1 illustrates a flow chart of the calculation of the command escape interval $IE_{CONSIG}$ such as is known from the aforementioned EP 0 750 920. In the basic cycle, which is implemented systematically, for example, every four cardiac cycles, the state of the activity sensor G is first discriminated and a determination is made whether there has been a modification of this sensor (i.e., a change in state). (Step 100.) If so, the escape interval $IE_G$ of the activity sensor G is calculated, the state of the sensor G is determined (Step 102) and the flow continues to the analysis of the effort sensor MV. (Step 104.) If not, the flow proceeds directly (from step 100) to the analysis of the state of the effort sensor Mv. (Step 104.) If there has been a modification of the state of the sensor MV, the escape interval $IE_{MV}$ of the sensor MV is calculated and the new state of this sensor is determined. (Step 106.)

Determining the state of the sensors is described in greater detailed in the aforementioned EP 0 705 920.

Once the two sensors are tested, whether or not there has been modification in the states of the sensors, the command escape interval $IE_{CONSIG}$ is calculated. (Step 108) Table 1 shows this calculation.

TABLE 1

| | | MV | | |
|---|---|---|---|---|
| | | REST | EFFORT | RECOVERY |
| G | REST | $IE_{BASE}$ | if $t < T_{MV}$ then $IE_{MV}$ else $IE_{BASE}$ | if $t < T_{MV}$ then $IE_{MV}$ else $IE_{BASE}$ |
| | EFFORT | if $t < T_G$ then $IE_G$ else $IE_{BASE}$ | $IE_{MV}$ | $IE_{MV}$ |
| | RECOVERY | if $t < T_G$ then $IE_G$ else $IE_{BASE}$ | $IE_{MV}$ | $IE_{MV}$ |

As shown in Table 1, the command escape interval $IE_{CONSIG}$ can take one of three values: $IE_{BASE}$ (the escape interval corresponding to the programmed basic frequency); $IE_G$ (the escape interval of sensor G); or $IE_{MV}$ (the escape interval of sensor MV).

If sensors G and MV are in the rest state, the command escape interval $IE_{CONSIG}$ is set equal to the escape interval $IE_{BASE}$ since a rest state is confirmed by the two sensors.

If the two sensors are in either the effort state or the recovery state, the command escape interval $IE_{CONSIG}$ is set equal to the escape interval $IE_{MV}$ of the sensor MV since an effort state is confirmed by the two sensors.

If the sensor G is in the rest state and the sensor MV is in a state other than the rest state, effort is not confirmed and the command escape interval $IE_{CONSIG}$ is defined as equal to the escape interval $IE_{MV}$ of the sensor MV during a limited time $T_{MV}$. Beyond this time, the command escape interval $IE_{CONSIG}$ is set equal to $IE_{BASE}$.

If the sensor MV is in the rest state and the sensor G is in a state other than the rest state, effort is not confirmed and the command escape interval $IE_{CONSIG}$ is defined as equal to the escape interval $IE_G$ of the activity sensor G during a limited time $T_G$. Beyond this time, the command escape interval $IE_{CONSIG}$ is set equal to $IE_{BASE}$.

The activity sensor G is typically an acceleration sensor (i.e., accelerometer). In the course of a significant effort, it responds in a specific (known) manner. However, activity sensor G is not considered a physiological sensor because it does not deliver a signal proportional to the level of effort. The effort sensor, the sensor MV, is physiological because it delivers, on the other hand, a signal that is proportional to the level of the effort. However, some external artifacts such as those of rhythmical movements in the bandwidth of respiration can mislead (i.e., fool) the sensor, which will indicate an exaggerated frequency of stimulation in relation to the level of effort.

To remedy this problem, lower and upper limits for the command escape interval $IE_{CONSIG}$ are defined according to the escape interval $IE_G$ of the activity sensor G. Indeed, the bandwidths of the two sensors MV and G do not superpose each other (i.e., no overlap of bandwidth)—the artifacts of one are filtered by the other. Since the command escape interval $IE_{CONSIG}$ is the value to which the enslaved escape interval $IE_{ASSER}$ (the period of stimulation determined by the function of enslavement) must tend, this last will be controlled by the escape interval $IE_G$ of the activity sensor G.

Figure 2:
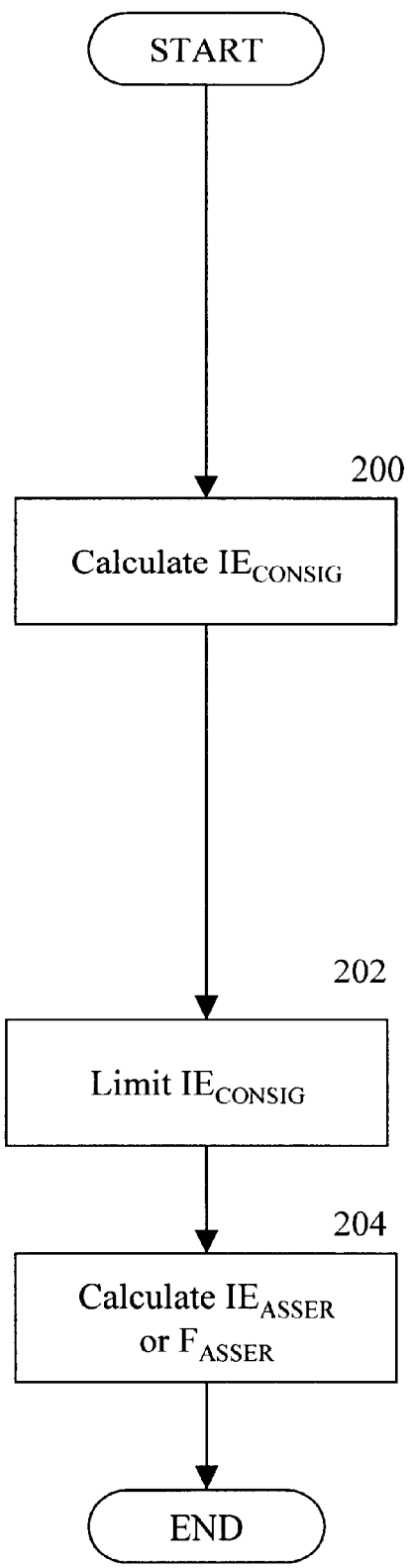
FIG. 2 illustrates a general flow chart of the functioning of the present invention.

FIG. 2 shows a general flow chart of the functioning of the present invention.

The first step is the calculation of the command escape interval $IE_{CONSIG}$ (Step 200) such as is known from the aforementioned EP 0 750 920 (see FIG. 1). After the limiting of the command escape interval $IE_{CONSIG}$ (Step 202), as will be described in more detail hereafter with respect to FIG. 4, the enslaved escape interval $IE_{ASSER}$ or the enslaved frequency $F_{ASSER}$ are calculated. (Step 204.) The calculation of the enslaved frequency is described in more detail in EP 0 750 920 and will not be further described here.

From the value of the escape interval $IE_G$ of the sensor G, a limit value for the escape interval $IE_{MV}$ of the sensor MV is defined. There are several manners to limit the escape interval $IE_{MV}$. Either an absolute limit can be defined by deducing a predefined constant period of the escape interval $IE_G$ of ($IE_G- X_{MS}$), or a relative limit can be defined by deducing a constant percentage predefined of the escape interval $IE_G$ of ($IE_G-\% IE_G$). Alternatively, the limit of the escape interval $IE_{MV}$ can also be defined as a function of the escape interval $IE_G$ of the activity sensor ($f(IE_G)$).

According to a preferred embodiment of the invention, two limits are defined, one for the lower (i.e., inferior) limitation of the command escape interval $IE_{CONSIG}$ ($IE_{LIMIT\_MV\_INF}$) and the other for the upper (i.e., superior) limitation of this interval ($IE_{LIMIT\_MV\_SUP}$)

Figure 3:
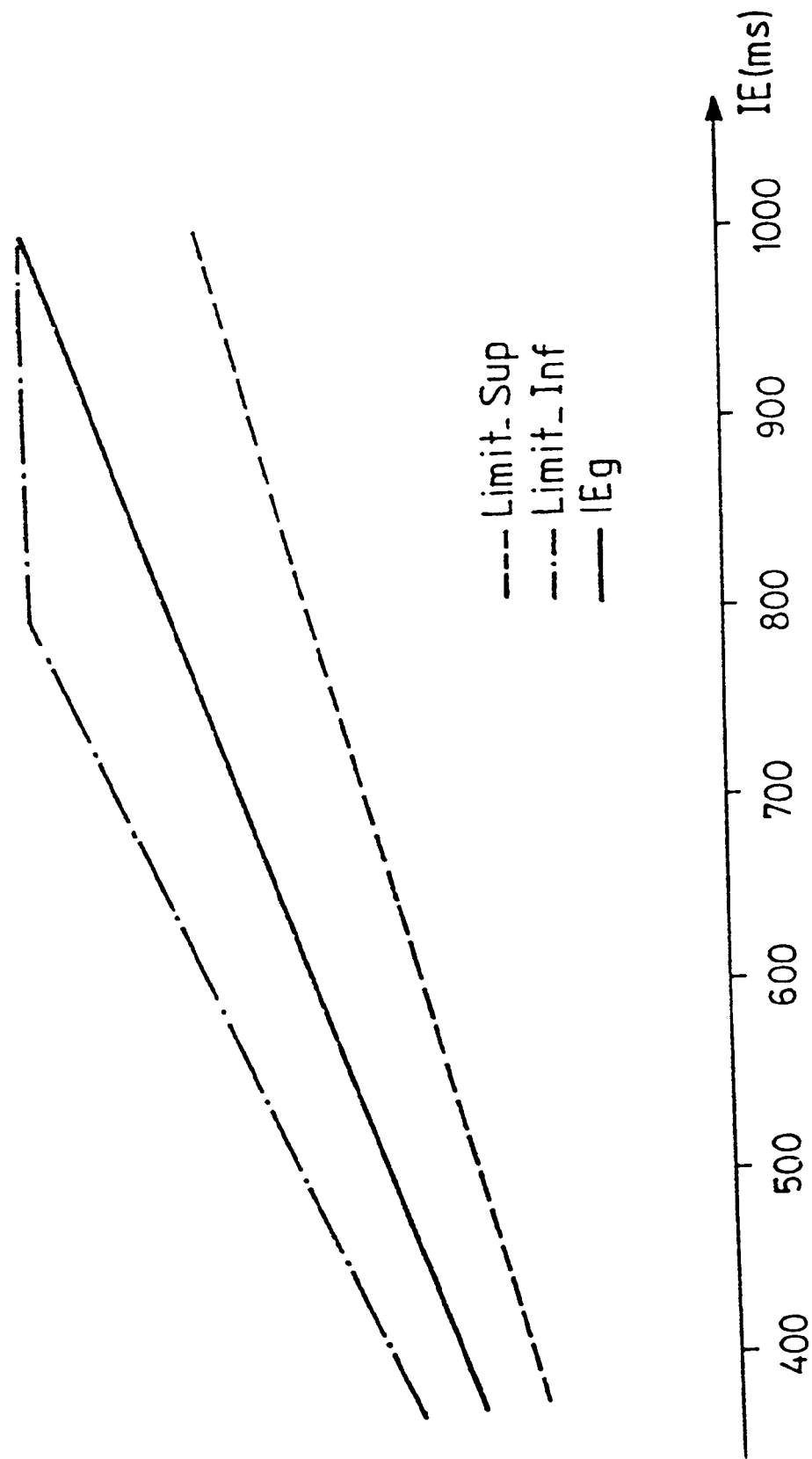
FIG. 3 illustrates the evolution of the limitation according to the escape interval defined by the activity sensor according to the present invention.

FIG. 3 shows the case of application of a relative limit according to the present invention.

Here, the lower and upper limits are defined as a percentage of the escape interval $IE_G$ of the activity sensor. The lower limit of the escape interval $IE_{MV}$ ($IE_{LIMIT\_MV\_INF}=IE_G-25\% IE_G$) and the upper limit of this interval ($IE_{LIMIT\_MV\_SUP}=IE_G+25\% IE_G$) are proportional to the escape interval $IE_G$ of the activity sensor.

Each time a modification of the escape interval $IE_G$ of the sensor G (see FIG. 1) is observed, the two limits $IE_{LIMIT\_MV\_INF}$ and $IE_{LIMIT\_MV\_SUP}$ of the escape interval $IE_{MV}$ of the effort sensor are redefined.

As soon as the command escape interval $IE_{CONSIG}$ (calculated according to the table 1) exceeds one of these limits, it is limited to that limit value.

Figure 4:
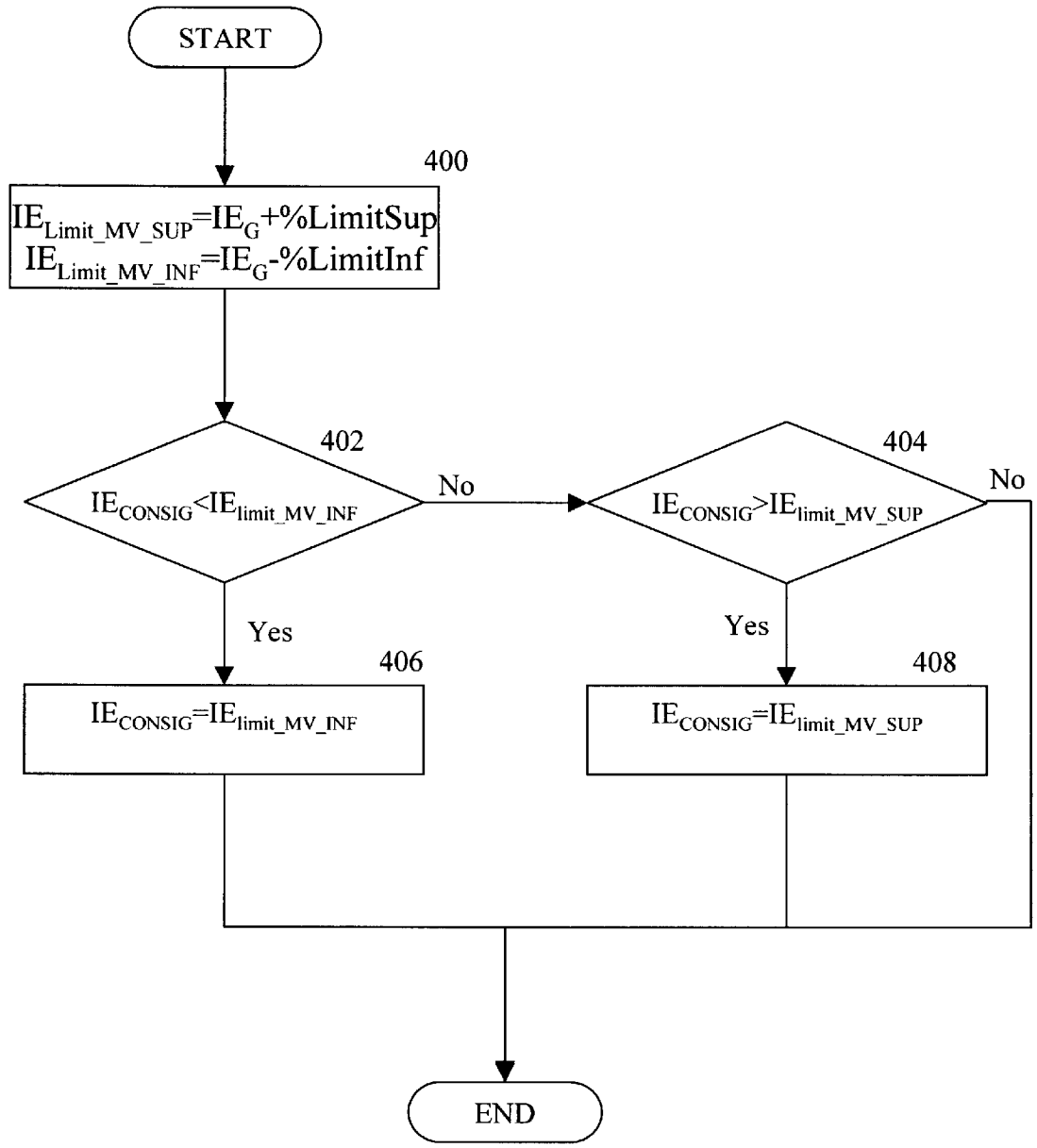
FIG. 4 illustrates limitation of the command escape interval according to the present invention.

FIG. 4 illustrates a comparison of the value of the command escape interval $IE_{CONSIG}$ with the lower and upper limits and the consequent limitation of $IE_{CONSIG}$.

In step 400, the lower and upper limits are defined. The command escape interval $IE_{CONSIG}$ is then compared to the lower (step 402) and upper (step 404) limits and, where the limits are exceeded, limited accordingly (steps 406, 408 respectively). Where within both limits, $IE_{CONSIG}$ is left unmodified (by the limits).

When the effort sensor alone determines an effort, the enslavement frequency can therefore increase during a predefined time $T_{MV}$ until the limit value. Beyond this time, if the effort is not yet confirmed by the activity sensor G, the enslavement frequency is decreased to the basic frequency corresponding to $IE_{BASE}$. Consequently, the enslavement frequency will be if, limited by the lower limit $IE_{LIMIT\_MV\_INF}$. for example, the escape interval $IE_G$ of the effort sensor is equal to the programmed basic interval of escape $IE_{BASE}$ (e.g., having a value of 1000 ms) and the relative predefined limit is 25% of $IE_G$, a maximum enslavement frequency of 60 000/(1000 ms −250 ms) or 80 bpm [i.e., beats per minute] is determined. The enslavement frequency is generally defined as the frequency of stimulation determined by the function of enslavement (=60 000 ms/period of enslavement).

In the course of an effort, the period of enslavement will be limited at each instant in relation to the activity sensor. For example, for an escape interval $IE_G$ of the activity sensor equal to 600 ms (100 bpm) and a limit of 25%, the minimal value of $IE_{MV}$ will be 450 ms (133 bpm).

Figure 5:
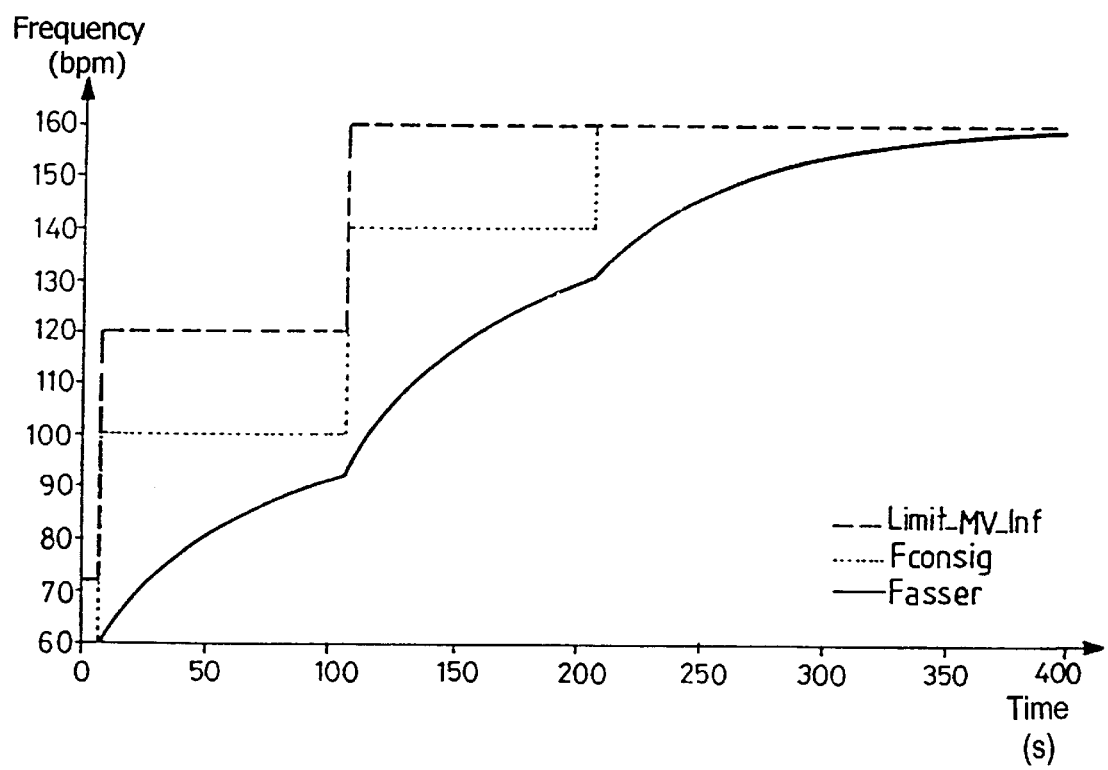
FIG. 5 illustrates the effect of limitation by the activity sensor by steps in a normal case interval according to the present invention.

FIG. 5 shows the normal case in which the lower limit of the escape interval IE ($IE_{LIMIT\_MV\_INF}$) is less than the command escape interval $IE_{CONSIG}$.

In FIG. 5, the command frequency $F_{CONSIG}$, is less than the frequency limit ($F_{LIMIT\_MV\_INF}$) and, consequently, the enslaved frequency $F_{ASSER}$ follows the command frequency $F_{CONSIG}$.

Figure 6:
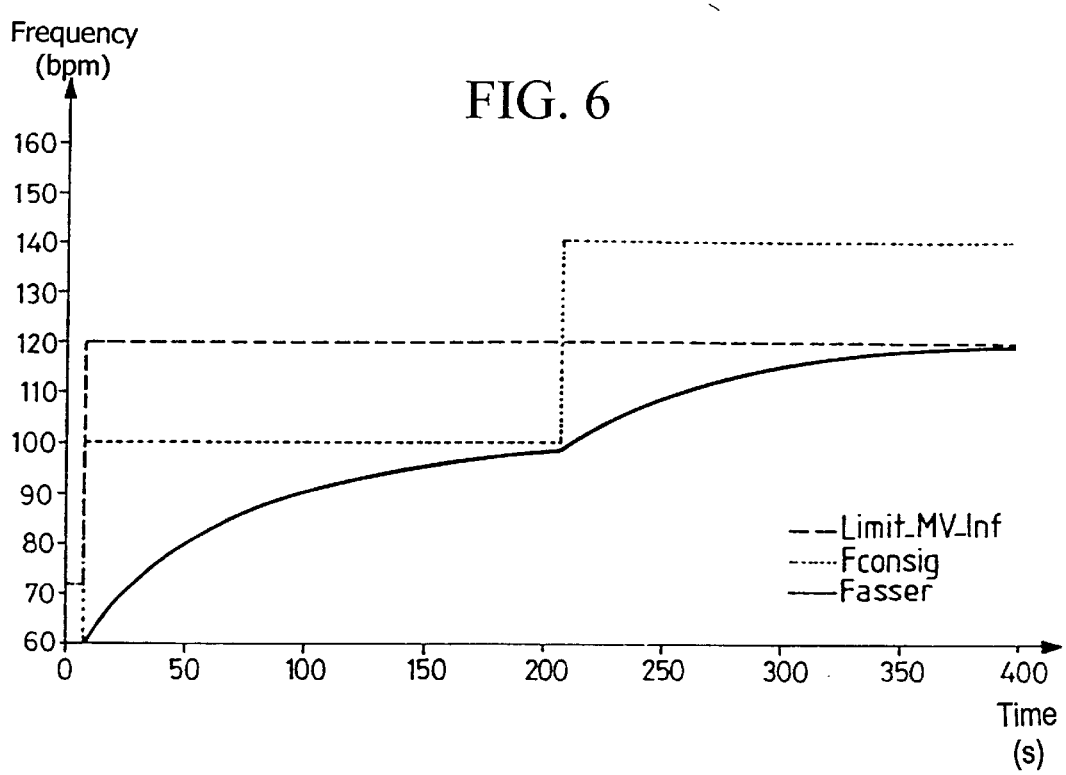
FIG. 6 illustrates the effect of limitation by the activity sensor by steps interval according to the present invention.

In the case of FIG. 6, the command frequency $F_{CONSIG}$ is greater than the frequency limit ($F_{LIMIT\_MV\_INF}$) during of the second step. The enslaved frequency $F_{ASSER}$ will therefore follow the limit frequency.

In another embodiment, the limitation of the command escape interval $IE_{CONSIG}$ is applied only in cases where effort sensor MV and activity sensor G are both in states other than the rest state. Thus the limitation would not be applied to an effort determined by only the effort sensor MV unconfirmed by the activity sensor G, for example, in the case of a stress.

In general manner, this principle can be extended to all sensors where one limits a first sensor by a second sensor (or limited by a combination of several sensors), the first sensor being preferably a physiological sensor and the second sensor being an activity sensor (i.e., an acceleration or pressure sensor).

Figure 7:
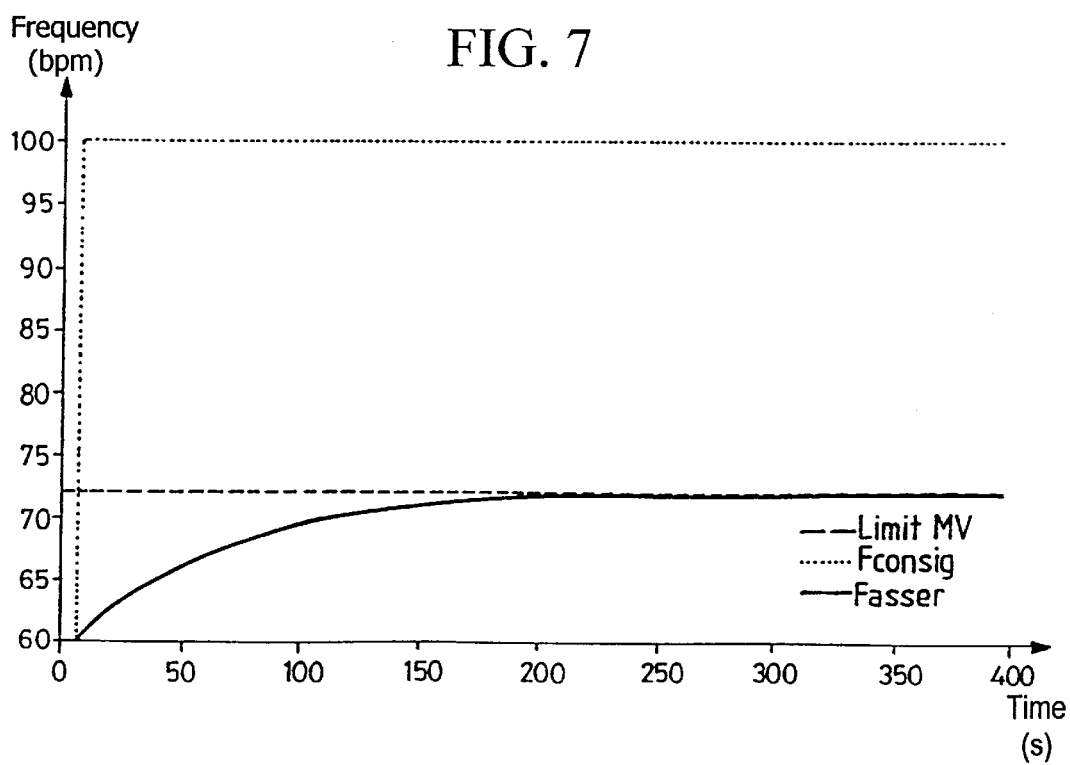
FIG. 7 illustrates the effect of limitation by the activity sensor interval according to the present invention.

According to a preferred embodiment of the present invention, cross control by the effort is anticipated. If the effort sensor MV detects an effort that is not detected by the activity sensor G, the enslavement frequency will be limited. FIG. 7 illustrates such an example. The time of enslavement on only one sensor can be suppressed before confirmation by the second.

The present invention has been described with reference to specific embodiments thereof. It will be understood by one skilled in the art that these are not exclusive embodiments, and while the foregoing description of illustrative embodiments discusses certain specificities, these enabling details should not be construed as limiting the scope of the invention, and it will be readily understood by those persons skilled in the art that the present invention is susceptible to many modifications, adaptations, and equivalent implementations without departing from this scope and without diminishing its advantages.

I claim:

1. An active implantable medical device having a control function enslaved to at least one physiological parameter comprising:

at least one effort sensor (MV) having a plurality of determinable states, the sensor measuring a primarily physiological parameter and delivering a signal which is a function of effort exerted by a patient bearing the device;

at least one activity sensor (G) having a plurality of determinable states, the sensor measuring a primarily physical parameter and delivering a signal indicative of the activity of the patient bearing the device;

means for determining the determinable states of the respective sensors;

means for identifying periodically a relative sequence of successive changes in the state of the respective sensors according to predetermined identification criteria;

means for analyzing periodically the relative sequence of successive changes in the state of the respective sensors according to predetermined analysis criteria;

means for determining a command escape interval ($IE_{CONSIG}$) controlling the control function of the device from the analyzed states of the sensors;

means for determining an escape interval of the activity sensor ($IE_G$); and means for limiting the command escape interval ($IE_{CONSIG}$) as a function of the escape interval of the activity sensor ($IE_G$).

2. The device of claim 1 wherein the means for limiting the command escape interval ($IE_{CONSIG}$) include limitations which correspond to the subtraction of a predefined constant percentage of the escape interval of the activity sensor ($IE_G$).

3. The device of claim 1 wherein the means for limiting the command escape interval ($IE_{CONSIG}$) include two limitations, a lower limit ($IE_{LIMIT\_MV\_INF}$) and an upper limit ($IE_{LIMIT\_MV\_SUP}$), which are applied to limit the command escape interval ($IE_{CONSIG}$).

4. The device of claim 3 wherein the means for analyzing further comprises means for determining whether the escape interval of the activity sensor ($IE_G$) has changed, and wherein the lower limit ($IE_{LIMIT\_MV\_INF}$) and the upper limit ($IE_{LIMIT\_MV\_SUP}$) are redefined each time the means for analyzing determines that the escape interval of the activity sensor ($IE_G$) has changed.

5. The device of claim 1 further comprising means for calculating an enslavement frequency as a function of the analyzed states of the sensors.

6. The device of claim 5 wherein one of the plurality of determinable states comprises an effort state, the means for determining the determinable states further comprises means for determining when the effort sensor detects an effort state and when the activity sensor does not detect an effort state, and the means for limiting the command escape interval ($IE_{CONSIG}$) further comprises means for limiting the enslavement frequency when the effort sensor (MV) detects an effort not detected by the activity sensor (G).

7. A method for controlling an active implantable medical device having a control function enslaved to at least one physiological parameter comprising the steps of:
    measuring a primarily physiological parameter and delivering a signal which is a function of effort exerted by a patient bearing the device;
    measuring a primarily physical parameter and delivering a signal indicative of the activity of the patient bearing the device;
    determining determinable states of the respective measurements;
    identifying periodically a relative sequence of successive changes in the respective states according to predetermined identification criteria;
    analyzing periodically the relative sequence of successive changes in the respective states according to predetermined analysis criteria;
    determining a command escape interval ($IE_{CONSIG}$) controlling the control function of the device from the analyzed states;
    determining an escape interval of the activity sensor ($IE_G$); and
    limiting the command escape interval ($IE_{CONSIG}$) to predetermined values as a function of the escape interval of the activity sensor ($IE_G$).

8. The method of claim 7 wherein the command escape interval ($IE_{CONSIG}$) is limited to predetermined values which correspond to the subtraction of a predefined constant percentage of the escape interval of the activity sensor ($IE_G$).

9. The method of claim 7 further comprising providing a lower limit ($IE_{LIMIT\_MV\_INF}$) and an upper limit ($IE_{LIMIT\_MV\_SUP}$) and limiting the command escape interval ($IE_{CONSIG}$) by said upper and lower limits.

10. The method of claim 9 wherein analyzing the relative sequence of successive states further comprises determining that the escape interval of the activity sensor ($IE_G$) is modified and in response thereto redefining the upper and lower limits.

11. The method of claim 7 wherein the control function is an enslavement frequency, measuring the primarily physiological parameter further comprises providing an effort sensor to obtain said signal, and the step of limiting the command escape interval ($IE_{CONSIG}$) also includes limiting the enslavement frequency when the effort sensor (MV) detects an effort not detected by the activity sensor (G).

12. An active implantable medical device programmed to perform the method of claim 7.

13. An active implantable medical device having a control function enslaved to at least one physiological parameter comprising:
    at least one effort sensor (MV) having a plurality of determinable states, the sensor measuring a primarily physiological parameter and delivering a signal which is a function of effort exerted by a patient bearing the device;
    at least one activity sensor (G) having a plurality of determinable states, the sensor measuring a primarily physical parameter and delivering a signal indicative of the activity of the patient bearing the device;
    means for determining the determinable states of the respective sensors;
    means for identifying periodically a relative sequence of successive changes in the state of the respective sensors according to predetermined identification criteria;
    means for analyzing periodically the relative sequence of successive changes in the state of the respective sensors according to predetermined analysis criteria;
    means for determining a command escape interval ($IE_{CONSIG}$) controlling the control function of the device from the analyzed states of the sensors; and
    means for limiting the command escape interval ($IE_{CONSIG}$) as a function of an escape interval of the activity sensor ($IE_G$);

14. A method for controlling an active implantable medical device having a control function enslaved to at least one physiological parameter comprising the steps of:
    measuring a primarily physiological parameter and delivering a signal which is a function of effort exerted by a patient bearing the device;
    measuring a primarily physical parameter and delivering a signal indicative of the activity of the patient bearing the device;
    determining determinable states of the respective measurements;
    identifying periodically a relative sequence of successive changes in the respective states according to predetermined identification criteria;
    analyzing periodically the relative sequence of successive changes in the respective states according to predetermined analysis criteria;
    determining a command escape interval ($IE_{CONSIG}$) controlling the control function of the device from the analyzed states; and
    limiting the command escape interval ($IE_{CONSIG}$) to predetermined values as a function of an escape interval of the activity sensor ($IE_G$);
    wherein one of the determinable states comprises a rest state and limiting the command escape interval ($IE_{CONSIG}$) is performed by applying the limitation of the command escape interval ($IE_{CONSIG}$) only where the physiological parameter is in a state other than the rest state.

* * * * *